United States Patent
Sivaprakasam et al.

(10) Patent No.: US 12,220,180 B2
(45) Date of Patent: Feb. 11, 2025

(54) ROBOTIC SURGERY SYSTEMS AND SURGICAL GUIDANCE METHODS THEREOF

(71) Applicant: Indian Institute of Technology Madras (IIT Madras), Chennai (IN)

(72) Inventors: Mohanasankar Sivaprakasam, Chennai (IN); Keerthi Ram, Chennai (IN); Manojkumar Lakshmanan, Chennai (IN)

(73) Assignee: Indian Institute of Technology Madras (IIT Madras), Chennai (IN)

( * ) Notice: Subject to any disclaimer, the term of this patent is extended or adjusted under 35 U.S.C. 154(b) by 618 days.

(21) Appl. No.: 17/415,645

(22) PCT Filed: Dec. 31, 2019

(86) PCT No.: PCT/IB2019/061459
§ 371 (c)(1),
(2) Date: Jun. 17, 2021

(87) PCT Pub. No.: WO2020/129034
PCT Pub. Date: Jun. 25, 2020

(65) Prior Publication Data
US 2022/0054199 A1   Feb. 24, 2022

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/30* (2016.02); *A61B 90/39* (2016.02); *B25J 13/089* (2013.01);
(Continued)

(58) Field of Classification Search
CPC . A61B 34/20; A61B 34/30; A61B 2034/2051; A61B 2034/2055; B25J 13/089; G06T 19/006
(Continued)

(56) References Cited

U.S. PATENT DOCUMENTS 8,694,075 B2 * 4/2014 Groszmann ............ A61B 6/488
382/128
9,547,940 B1 * 1/2017 Sun .......................... G06T 7/344
(Continued)

OTHER PUBLICATIONS

International search report and written opinion for application No. PCT/IB2019/061459 mailed on May 20, 2020, 9 pages.

*Primary Examiner* — Boniface N Nganga
(74) *Attorney, Agent, or Firm* — Convergence Intellectual Property Law P.C.; Jonathan Garfinkel

(57) ABSTRACT

The invention in its various embodiments relates to a method of providing surgical guidance and targeting in robotic surgery systems. The method utilizes data from a navigation system in tandem with 2-dimensional (2D) intra-operative imaging data. 2D intra-operative image data is superimposed with a pre-operative 3-dimensional (3D) image and surgery plans made in the pre-operative image coordinate system. The superimposition augments real-time intraoperative navigation for achieving image guided surgery in robotic surgery systems. Also, a robotic surgery system that incorporates the method of providing surgical guidance and targeting is disclosed. The advantages include minimizing radiation exposure to a patient by avoiding intra-operative volumetric imaging, mobility of tools, imager and robot in and out of the operating space without the need for re-calibration, and relaxing the need for repeating precise imaging positions.

8 Claims, 9 Drawing Sheets

(51) Int. Cl.
| | |
|---|---|
| *A61B 34/30* | (2016.01) |
| *A61B 90/00* | (2016.01) |
| *B25J 13/00* | (2006.01) |
| *B25J 13/08* | (2006.01) |
| *G06T 7/00* | (2017.01) |
| *G06T 7/246* | (2017.01) |
| *G06T 7/80* | (2017.01) |
| *G06T 11/00* | (2006.01) |
| *G06T 19/00* | (2011.01) |

(52) U.S. Cl.
CPC ............... *G06T 7/248* (2017.01); *G06T 7/80* (2017.01); *G06T 11/003* (2013.01); *G06T 19/006* (2013.01); *A61B 2034/2051* (2016.02); *A61B 2034/2055* (2016.02); *A61B 2034/2065* (2016.02); *A61B 2090/374* (2016.02); *A61B 2090/3762* (2016.02); *A61B 2090/378* (2016.02); *G06T 2207/10081* (2013.01); *G06T 2207/10088* (2013.01); *G06T 2207/10116* (2013.01); *G06T 2207/10132* (2013.01); *G06T 2207/30004* (2013.01); *G06T 2207/30204* (2013.01); *G06T 2211/424* (2013.01)

(58) Field of Classification Search
USPC .......................................................... 382/103
See application file for complete search history.

(56) References Cited

U.S. PATENT DOCUMENTS

| | | | |
|---|---|---|---|
| 11,790,554 B2* | 10/2023 | Woods | .................. G06F 3/0482 |
| | | | 382/103 |
| 2003/0130576 A1 | 7/2003 | Seeley et al. | |
| 2005/0015005 A1 | 1/2005 | Kockro | |
| 2006/0291710 A1* | 12/2006 | Wang | ...................... G06T 15/08 |
| | | | 382/154 |
| 2008/0269588 A1 | 10/2008 | Csavoy et al. | |
| 2011/0052008 A1 | 3/2011 | Holsing et al. | |
| 2013/0231557 A1 | 9/2013 | Li et al. | |
| 2014/0334709 A1* | 11/2014 | Siewerdsen | ............... G06T 7/32 |
| | | | 382/132 |
| 2016/0078633 A1* | 3/2016 | Tahmasebi Maraghoosh | ............. |
| | | | G06T 7/174 |
| | | | 382/131 |
| 2016/0191887 A1 | 6/2016 | Casas | |
| 2018/0168740 A1 | 6/2018 | Ryan et al. | |

* cited by examiner

ROBOTIC SURGERY SYSTEMS AND SURGICAL GUIDANCE METHODS THEREOF

CROSS-REFERENCES TO RELATED APPLICATIONS

This application is a 35 U.S.C. § 371 national stage filing of PCT Patent Application Number PCT/IB2019/061459, filed Dec. 31, 2019, which claims priority to Indian provisional patent application No. 201841048137 entitled Method for utilizing a navigation system in tandem with traditionally used intra-operative imaging in orthopaedic surgery filed on 19 Dec. 2018.

FIELD OF THE INVENTION

The disclosure relates generally to image guided surgery and in particular to providing surgical guidance and targeting in robotic surgery systems.

DESCRIPTION OF THE RELATED ART

Robotic surgery is an emerging technology that performs minimally invasive surgeries. The step involved in robotic surgery includes obtaining preoperative images of a region to be operated on a patient, transforming the preoperative image data to a coordinate system employed by the robot. Plans are made in the pre-operative image coordinate system and subsequently a medical tool is controlled robotically based on information in the preoperative image. One of the important requirements in robotic surgery is enabling the robot to navigate the surgical tool based on the preoperative image data. Navigating the surgical tool accurately relies on precise registration between the preoperative data set and the coordinate system of the surgical robot.

Registration accuracy is limited by the resolution of each of the different coordinate systems, and the measurement precision of the navigation system. Further registration is desynchronized by intra-operative disturbance of each coordinate system, manual handling, physical movements due to forces being applied at the surgical site, relocation and reintroduction of mobile tools and imaging systems. Further, there are limitations in the acquisition, modality and protocol brought into each coordinate system. For example the pre-operative image might have captured the patient in the supine position, whereas intra-operatively the patient could be in the prone position, therefore registration involves computing a non-trivial relationship. The navigation system is limited by line of sight, whereas the pre-operative image has subcutaneous information and does not suffer occlusion. The intra-operative imaging modality such as fluoroscopy permits high resolution cross-sectional or projective views, but reduced to 2D, and mapping to 3D is underdetermined and non-unique.

The U.S. Pat. No. 7,010,080B2 discloses method and apparatus for automatic marker-free registration of a pre-operative 3d image with intra-operative fluoroscopic 3d reconstruction. The U.S. Pat. No. 8,010,177B2 discloses a method in which the reference marker might be moved and re-planted at different positions of the spine in order to remain close to the surgical site "Standardized evaluation methodology for 2-D-3-D registration", van de Kraats et al (2005), registration. IEEE Trans. Med. Imag. 24 (9), 1177-1189, relates to an evaluation methodology that uses the calibrated geometry of a 3-D rotational X-ray (3DRX) imaging system in combination with image-based 3-D-3-D registration for attaining a highly accurate gold standard for 2-D X-ray to 3-D MR/CT/3DRX registration. "Geometric calibration of a mobile C-arm for intraoperative cone-beam CT," M. J. Daly et al (2008) Med Phys, vol. 35, no. 5, pp. 2124-2136 describes a geometric calibration method that determines a complete description of source-detector geometry adapted to a mobile C-arm for cone-beam computed tomography.

System and methods are disclosed that provides surgical guidance and targeting in robotic surgery systems.

SUMMARY OF THE INVENTION

In various embodiments a method of providing surgical guidance and targeting in robotic surgery systems is disclosed. The robotic surgery systems include an imager that has a source, a detector having a marker and a navigation system that has a tracker. The method includes the steps of capturing by an imaging system pre-operative image data of a patient at predetermined positions and orientations. A 3D pre-operative image data is reconstructed from the captured pre-operative image data using a processing system. 2D intra-operative image data of the patient are captured at the predetermined positions and orientations of the imager during a surgical procedure. The 2D intra-operative image data and the navigation system data in real time during the surgical procedure are registered to track the position of one or more navigated or robotically articulated surgical tools. Further the 2D intra-operative image data are registered with the 3D pre-operative image data. In various embodiments the method augments intra-operative image data with a rendering of the 3D pre-operative image data that is in registration with the real time intra-operative 2D image data.

In various embodiments registering the 2D intra-operative image data with the 3D pre-operative image data includes calibrating one or more intrinsic parameters of the imager. Extrinsic calibration of the imager is performed to localize the detector image plane in 3D with respect to a surgical site. In various embodiments the calibration includes the steps of capturing two or more images of a space calibration object placed on an operating surface, using the imager. The detector is positioned at two or more predetermined locations and orientations. The object includes a spiral arrangement of reference indices embedded around a radio transparent cylindrical structure and arranged around a camera axis. The position and displacement of the detector is recorded by a tracker attached to the detector, for each image capture. The location of the reference indices is identified in each capture.

In various embodiments a projection is computed iteratively from a spiral canonical 3d coordinate system to each of the captured images and an Euler rotation for each image is obtained. A transform that links the computed projections and the tracker recorded positions and displacements of the detector are further obtained. In various embodiments the pre-operative image data is positioned in the spiral canonical 3D coordinate system and one or more digital radiographic re-projections (DRR) are applied to obtain a 2D projection of the preoperative volume that is aligned with the 2D intra-operative images.

In various embodiments the space calibration object is a cylindrical object and is placed with a first reference index kept proximal to the tracker. In various embodiments the cylindrical object has a reference marker placed proximal to the first reference index. In various embodiments identifying the location of the reference indices is based on image processing techniques selected from thresholding or Hough transform.

In various embodiments the projection is done by iterative optimization techniques selected from steepest descent, least-squares minimization, or Frobenius-norm minimization. In various embodiments the positioning of the pre-operative volume in the spiral canonical 3D coordinate system and applying one or more digital radiographic re-projections (DRR) does not require placement of markers on the patient.

In various embodiments the imaging system is a C-arm apparatus comprising x-ray modality or ultrasound or both. In various embodiments the imaging system includes a pre-operative volumetric imaging modality and is selected from CT scan or MRI scan. In various embodiments the navigation system is an optical navigation system or an electro-magnetic system.

In various embodiments robotic surgery system is disclosed. The system includes an imaging system, a navigator system, computing system and a display system. The imaging system includes an imaging modality that is configured to capture pre-operative 2D images of a patient at predetermined positions and orientations and reconstruct a 3D pre-operative image from the obtained 2D images. An imager having a source, a detector and a marker attached to the detector. In various embodiments the imager is configured to be fixed at one or more positions and orientations and may capture 2D intra-operative image data of a patient during a surgical procedure. The system includes a navigator system that had a tracker and is configured to obtain navigator data that includes position information of one or more navigated or robotically articulated surgical tools. The computing system includes a memory module and a processing module coupled to the memory module. The processing module is configured to register the 2D intra-operative image data and the navigation system data in real time during the surgical procedure to track the position of tools. The 2D intra-operative image data is registered with the 3D pre-operative image and the 2D intra-operative image data is augmented with a rendering of the 3D pre-operative image data that is in registration with the real time intra-operative 2D image data. In various embodiments the display device is configured to display the rendering of the 3D pre-operative image data that is in registration with the real time intra-operative 2D image data and the position of the tools.

In various embodiments to register the 2D intra-operative image data with the 3D pre-operative image data, the processing module is configured to calibrate one or more intrinsic parameters of the imager and perform extrinsic calibration of the imager to localize the detector image plane in 3D with respect to a surgical site. Further two or more images of the patient is obtained using the imager with the detector positioned at the predetermined locations and orientations. In various embodiments the pre-operative volume is aligned in the spiral canonical 3D coordinate system and one or more digital radiographic re-projections (DRR) is applied to obtain a 2D projection of the preoperative volume that is aligned with the 2D intra-operative images.

In various embodiments to perform extrinsic calibration of the imager the processing module is configured to capture two or more images of a space calibration object placed on a surface. The detector is positioned at two or more predetermined locations and orientations. The object includes a spiral arrangement of reference indices embedded around a radio transparent cylindrical structure and arranged around a camera axis. In various embodiments the position and displacement of the detector are recorded by a tracker for each image capture. The location of the reference indices are identified in each capture. A projection is computed iteratively from a spiral canonical 3d coordinate system to each of the captured images and an Euler rotation for each image is obtained. In various embodiments a transform that links the computed projections and the tracker recorded positions and displacements of the detector are obtained.

In various embodiments the space calibration object is a cylindrical object and is placed with a first reference index kept proximal to the tracker. In various embodiments the cylindrical object has a reference marker near the first reference index. In various embodiments to identify the location of the reference indices the processing module is configured to apply image processing techniques selected from thresholding or Hough transform.

In various embodiments to compute a projection the processing module is configured to apply iterative optimization techniques selected from steepest descent, least-squares minimization, or Frobenius-norm minimization. In various embodiments the imager is a C-arm apparatus comprising x-ray modality or ultrasound or both. In various embodiments the imaging modality is selected from CT scan or MRI scan. In various embodiments the navigation system is an optical navigation system or an electro-magnetic system.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Figure 1:
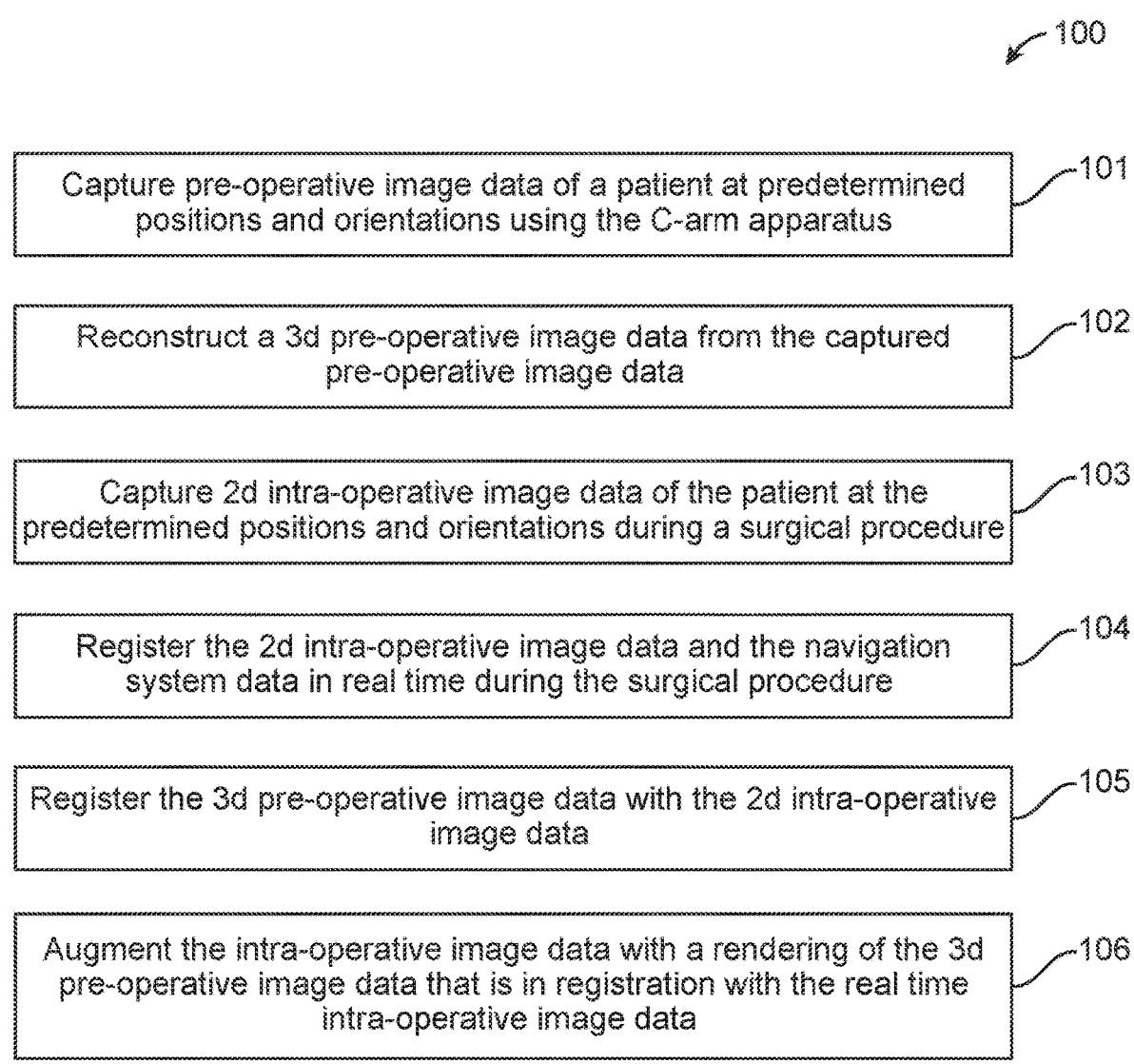
FIG. 1 illustrates a method of providing surgical guidance and targeting in robotic surgery systems.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The invention in its various embodiments relates to a method of providing surgical guidance and targeting in robotic surgery systems. The method utilizes data from a navigation system in tandem with 2-dimensional (2D) intra-operative imaging data. In various embodiments the method includes superimposing the 2D intra-operative image data with a pre-operative 3-dimensional (3D) image and surgery plans made in the pre-operative image coordinate system. The superimposition augments real-time intraoperative navigation for achieving image guided surgery in robotic surgery systems. Also, a robotic surgery system that incorporates the method of providing surgical guidance and targeting is disclosed.

In various embodiments a method 100 for providing surgical guidance and targeting in robotic surgery systems is disclosed. The robotic surgery system includes an imager that may be positioned at any position and orientation. The imager includes a source and a detector that has a marker attached to it. The robotic system also includes a navigation system that has a tracker, and a processing system. In various embodiments the method 100 includes capturing pre-operative image data of a patient in step 101. The pre-operative image data is obtained at predetermined positions and orientations of an imaging system. In one embodiment the imaging system for capturing the pre-operative image data may include an imaging device that can be moved and fixed at predetermined positions and orientations. In another embodiment the imaging system may include a plurality of imaging devices that may be fixed at predetermined positions and orientations or can be moved to the predetermined positions and orientations. In step 102 a 3D pre-operative image data is reconstructed from the captured pre-operative image data using a processing system that receives the inputs from the imaging devices or plurality of imaging devices. The 3D pre-operative image data are the pre-operative volumetric data that is required for registration purposes.

In various embodiments in step 103, the method includes capturing 2D intra-operative image data of the patient lying on the operating table during a surgical procedure. The imager is positioned at the predetermined positions and orientations to capture the 2D images of the patient. In step 104 the 2D intra-operative image data of the patient and the navigation system data is registered in real time during the surgical procedure. This is done to track the position of one or more navigated or robotically articulated surgical tool involved in the surgical procedure. In step 105 the 2D intra-operative image data is registered with the 3D pre-operative image data of the patient. In step 106 the intra-operative image data is augmented with a rendering of the 3D pre-operative image data that is in registration with the real time intra-operative 2D image data.

Figure 2A:
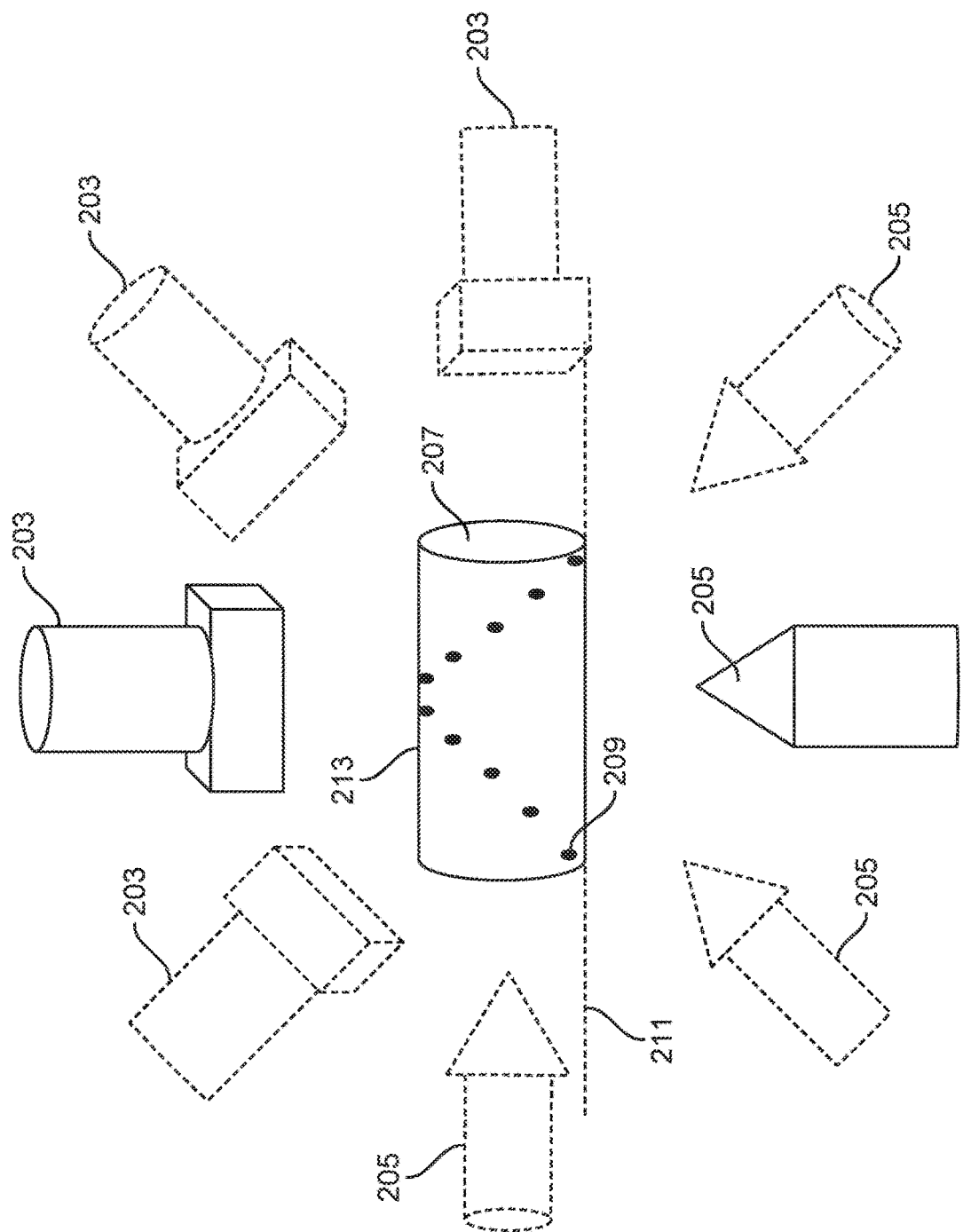
FIG. 2A illustrates the method performing extrinsic calibration of the imager with a cylindrical space calibration object.

In various embodiments the method of registering the 2D intra-operative image data with the 3D pre-operative image data includes calibrating one or more intrinsic parameters of the imager. The intrinsic parameters may include the image center, and the focal length of the imager. The available parameters of the imager are the source-detector distance, and the pixel spacing. The objective of performing intrinsic calibration of the c-arm is to establish invariant parameters that may interplay with extrinsic (positioning-dependent) parameters to obtain the scene projections. In various embodiments extrinsic calibration of the imager is performed. This is done to localize the detector image plane in 3D with respect to the surgical site. The method further includes performing extrinsic calibration. The objective of extrinsic calibration is to localize the detector image plane in 3d with respect to the surgical site. This depicts the plane projecting upon which would produce the imaged shot. This plane is given by the composition of the intrinsic parameter matrix and an Euler transform operating on the virtual camera plane [I|0], and rotating it to the set position. In various embodiments extrinsic calibration is performed by capturing two or more images of a space calibration object placed on a surface as shown in FIG. 2A. The detector 205 of the imager is positioned at two or more predetermined locations and orientations. In various embodiments the space calibration object 207 is a spiral arrangement of reference indices 209 that are embedded around a radio transparent cylindrical structure 213 and is arranged around a camera axis. The object by its design produces a canonical coordinate system by the location and orientation of the imager, where the i-th reference index has the coordinate $$x_i = r\cos(\theta_i)$$
$$y_i = -r\sin(\theta_i)$$
$$z_i = hx_i - \frac{L}{2}$$

with h being the vertical spacing between the reference indices, and L the length of the cylinder. In various embodiments the reference indices wind around the z-axis and the centroid of the location of the reference indices is the origin. In various embodiments the direction cosines of the space set up by this object are as follows: y-axis, vertical downward, z-axis that coincides with the spiral axis, x-axis that represents right to left in the head-first prone orientation of a patient, with head facing the tracker.

Figure 2B:
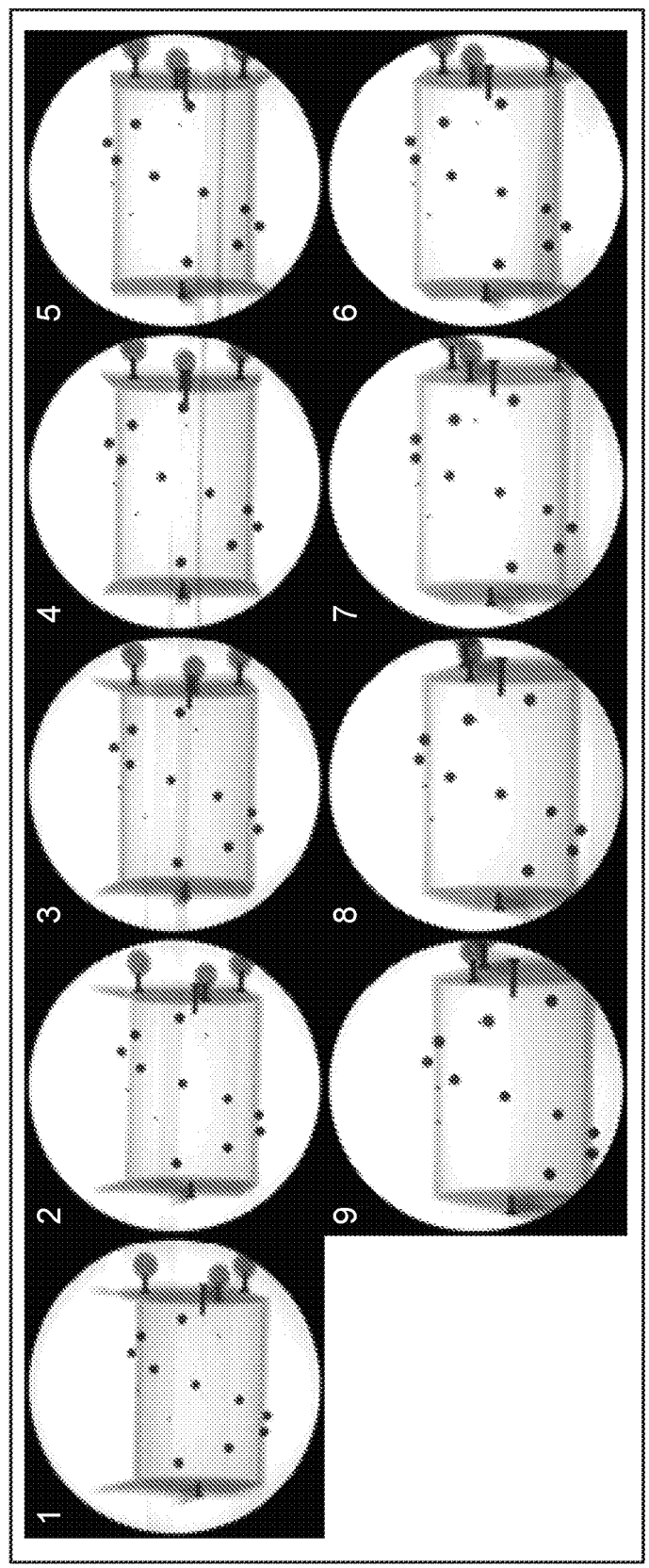
FIG. 2B shows fluoroscopy shots of the spiral object showing the radio-opaque reference indices.

For each image capture the position and displacement of the detector 205 are recorded by the tracker. The captured images appear as 2D projections of the object as shown in FIG. 2B. The location of the reference indices 209 are identified in each capture. Projection from a spiral canonical 3D coordinate system to the imaged 2D locations of the reference indices is computed iteratively to each of the captured images, that may be expressed by the equation x=PX, P is a 3×4 matrix which is a composition of the imaging device intrinsics 3×3 matrix, the extrinsics 3×4 matrix and an Euler transform 4×4 matrix. In some embodiments P has n number of degrees of freedom that requires a minimum of m correspondences in 3D. In various embodiments an Euler rotation for each image is obtained. In various embodiments a transform that links the computed projections and the tracker recorded positions and displacements of the detector are obtained.

In various embodiments the pre-operative volumetric data is aligned in the spiral canonical 3D coordinate system and one or more digital radiographic re-projections (DRR) are applied on the 3D data to obtain a 2D projection of the preoperative volume that is aligned with the 2D intra-operative images.

In various embodiments the location of the reference indices is identified based on image processing techniques selected from thresholding or Hough transform. In various embodiments iterative optimization techniques are used to compute a projection from a spiral canonical 3d coordinate system to each of the captured images. The iterative optimization techniques are selected from steepest descent, least-squares minimization, or Frobenius-norm minimization.

In various embodiments the positioning the pre-operative volume in the spiral canonical 3D coordinate system and applying one or more digital radiographic re-projections (DRR) is a non-invasive procedure. In various embodiments the non-invasive procedure does not require placing markers, pins, passive or active trackers or fiducials on the patient body. In some embodiments the imaging system is a C-arm apparatus comprising x-ray modality or ultrasound or both. In various embodiments the imaging system includes a pre-operative volumetric imaging modality. In one embodiment the imaging modality is CT scan. In another embodiment the imaging modality is MRI scan. In various embodiments the navigation system is an optical navigation system or an electro-magnetic system.

In various embodiments the method achieves positioning a robotic end effector, translating a virtual plan made in image space, to physical actuation, by directing a multi-axis surgical robotic arm.

Figure 3A:
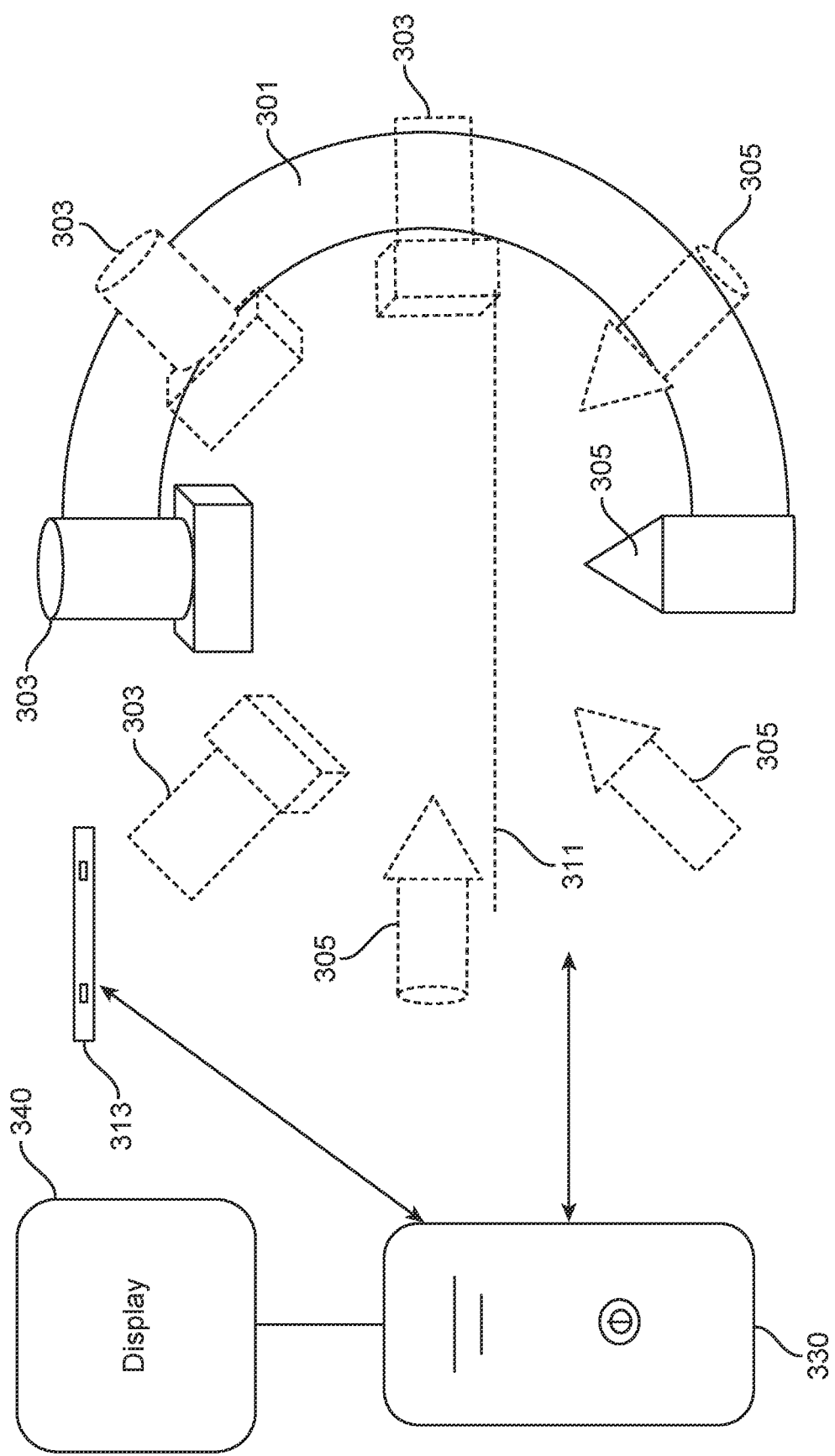
FIG. 3A illustrates the robotic surgery system.
Figure 3B:
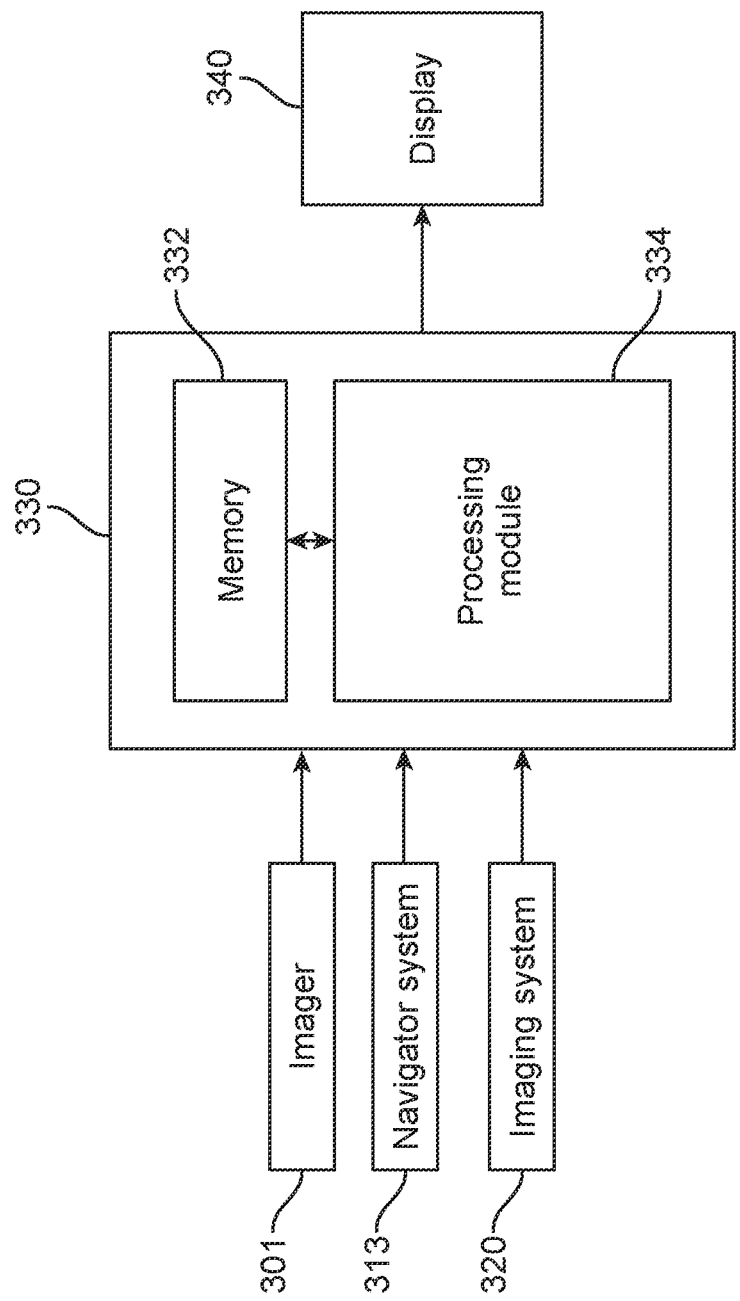
FIG. 3B illustrates the computing system in the robotic surgery system.

In various embodiments a robotic surgery system is disclosed. The system includes an imaging system configured to capture pre-operative images of a patient, an imager, a navigator system and a computing system. The imaging system has an imaging modality and a processor. The imaging modality is configured to capture pre-operative 2D images of a patient at predetermined positions and orientations. The processor is configured to reconstruct a 3D pre-operative image from the obtained 2D images. In various embodiments the imager 301 as shown in FIG. 3 includes a source 303, and a detector 305. In various embodiments a marker is attached to the detector. The imager 303 is fixed at one or more positions and orientations. The imager is configured to capture 2D intra-operative image data of a patient during a surgical procedure at each position and orientation. In various embodiments the navigator system 313 has a tracker and is configured to obtain navigation system data that includes the position information of tools.

In various embodiments the computing system 330 includes a memory module 332 and a processing module 334 coupled to the memory module 332. The processing module 334 receives input data from the imager and the navigator system. In various embodiments the pre-operative image data is stored in the memory module 332. In various embodiments the processing module 334 is configured to register the 2D intra-operative image data and the navigation system data in real time during the surgical procedure to track the position of tools. In various embodiments the processing module then registers the 2D intra-operative image data with the 3D pre-operative image. In various embodiments the processing module augments the 2D intra-operative image data with a rendering of the 3D pre-operative image data that is in registration with the real time intra-operative 2D image data. In various embodiments the display device 340 is configured to display the rendering of the 3D pre-operative image data that is in registration with the real time intra-operative 2D image data and the position of the tools.

In various embodiments to register the 2D intra-operative image data with the 3D pre-operative image data, the processing module is configured to initially calibrate one or more intrinsic parameters of the imager. Extrinsic calibration of the imager is performed to localize the detector image plane in 3D with respect to a surgical site. In various embodiments the processing module is configured to receive two or more image data of the patient that is captured using the imager. The images are obtained by positioning the detector at the predetermined locations and orientations. In various embodiments the processing module is configured to register a pre-operative volume by reconstructing a 3D image from the obtained two or more images and position the pre-operative volume in the spiral canonical 3D coordinate system. Further the module applies one or more digital radiographic re-projections (DRR) to the registered data to obtain a 2D projection of the preoperative volume that is aligned with the 2D intra-operative images.

In various embodiments the system uses a space calibration object as described earlier to perform extrinsic calibration of the imager. In various embodiments the space calibration object is a cylindrical object. In various embodiments the imager is a C-arm apparatus comprising x-ray modality or ultrasound or both. In one embodiment when the intra-operative imaging modality is ultrasound, registration is done by positioning the ultrasound plane into the pre-operative volume. The method of registration is selected from manual landmark registration, modality simulation, coarse registration followed by matching of surfaces or objects, or other methods used for registering ultrasound to CT volume. This is more suited for minimally invasive and epidural surgical and pain management procedures. In various embodiments the imaging modality is selected from CT scan or MRI scan. The navigation system is an optical navigation system or an electro-magnetic system.

The advantages of the disclosed method include minimizing radiation exposure to the patient. This is achieved by avoiding intra-operative volumetric imaging. The method do not include placing markers, pins, passive or active trackers or fiducials on the patient body. Also, the method permits mobility of tools, imager and robot in and out of the operating space, without the need for re-calibration, and relaxing the need for repeating precise imaging positions. Also, the invention achieves adequate precision in sensing of patient coordinates using potentially imprecise manually handling of imager (c-arm), with potential repositioning, avoiding the need for robotic actuation of the imager.

EXAMPLE

Example. 1: Surgical Guidance Method in Robotic Surgery Performed at the Lumbar Spine Region The source of the intra-operative mobile C-arm was kept under the table. The position of the C-arm is tracked using an optical marker attached to the detector. The c-arm was calibrated for its intrinsic parameters—specifically the image center, and the focal lengths, assuming the model of a standard pinhole projective camera. The available parameters of the c-arm are the source-detector distance (which is typically in the order of 1000 mm), and the pixel spacing in mm (typically 0.2 to 0.8 mm, image intensifier magnification-dependent).

Extrinsic calibration of the imager was performed. The objective of extrinsic calibration is to localize the detector image plane in 3D with respect to the surgical site. The extrinsic calibration depict the plane projecting upon which would produce the imaged shot. This plane is given by the composition of the intrinsic parameter matrix and an Euler transform operating on the virtual camera plane [I|0], and rotating it to the set position. To perform this calibration from multiple views requires a known space calibration object to be placed in the scene. The space calibration object has a specific spiral arrangement of ball bearings, to ensure unique traceability of each ball bearing across various detector poses. The spiral arrangement was made with 10 ball bearings wound counter-clockwise from −90 degree (as seen from the tracker), going around the camera axis and away from the camera. The object was placed on the surgical table, with the spiral axis along the cranio-caudal axis with ball-1 placed close to the tracker. The spiral was embedded around a radio-transparent cylindrical structure. A reference marker was placed close to the face of the cylinder close to ball-1.

Figure 4A:
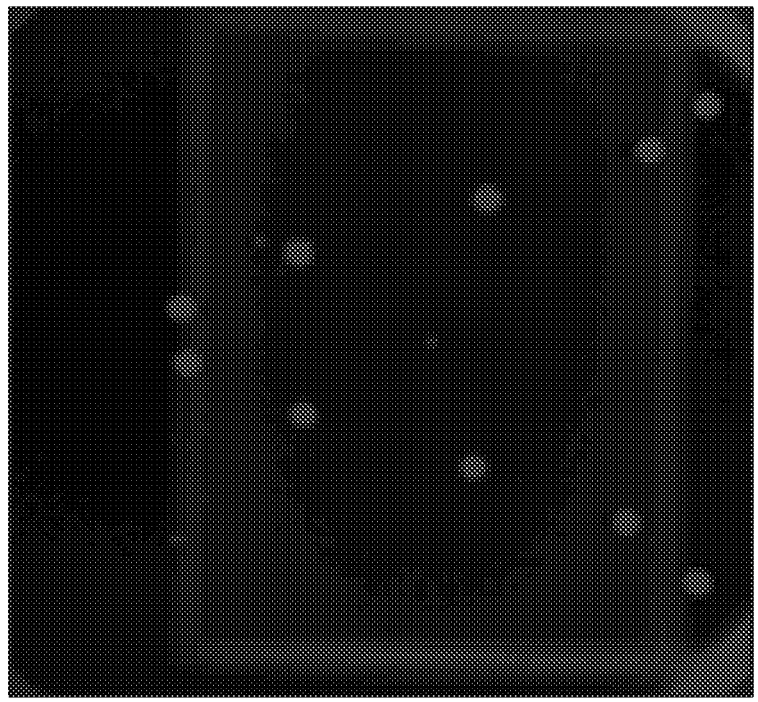
FIG. 4A illustrates shots appearing as 2D projections of the spiral object when taken at roughly equi-spaced poses with this object placed stationary under the c-arm

Shots were taken at roughly equi-spaced poses with this object placed stationary under the c-arm, and also recording the tracker position of the detector and corresponding to each shot. The shots appeared as 2D projections of the spiral object as shown in FIG. 4A. The location of the balls in each shot was found. Image processing techniques were used to automatically detect the location of the balls. The ball locations thus found in pixels were represented in mm by knowing the spacing and scale as set during imaging.

A projection from the canonical spiral-established 3D coordinate system to each of the shots was computed next. This may be done by one of a few common ways. The specific setup that was achieved was a correspondence between a canonical 3D point set to the imaged 2D locations of the balls, that is expressed by the equation x=PX; in homogeneous coordinates, P is a 3×4 matrix which is a composition of the camera intrinsic (3×3) the 3×4 matrix [I|0] and an Euler transform (4×4). P has 11 degrees of freedom, and requires minimum of 4 correspondences in 3D. The setup has up to 10 correspondences and provided an over-determined system of equations that was solved using iterative optimization approach.

Figure 4B:
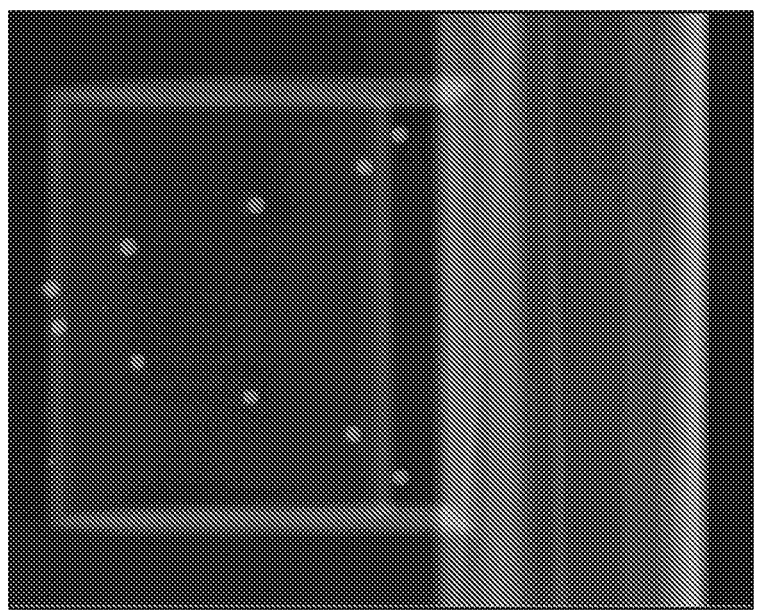
FIG. 4B illustrates registration between the intra-operative imaging and navigation system data.

Having solved for each pose independently, the intrinsic parameters was factored out to obtain the Euler rotation to each pose and matched with the tracker information of the pose of the detector. The reference marker being attached to the detector, has a rigid relationship with the detector pose. This relationship can be factorized out from the different obtained poses, as the common rigid transform linking the computed projective pose to the tracker observed quaternion and displacement. The registration between the intra-operative imaging and navigation system was completed as shown in FIG. 4B.

Utilizing the calibration performed above the pre-operative image was registered with the intra-operative scene/patient body. The c-arm was positioned precisely at the same locations at which the spiral calibration was done, The patient was imaged at this position. Using only such shots at the calibrated poses, structure-from-motion techniques were applied to reconstruct 3D from the different shots.

Figure 5A:
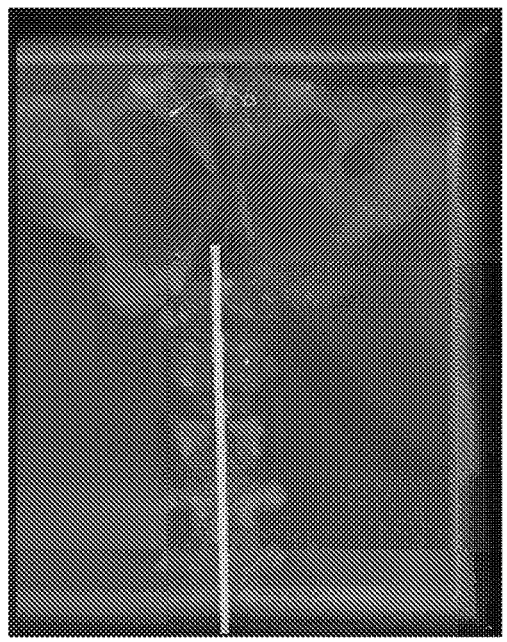
FIG. 5A illustrates the AP (anterio-posterior) imager shot of a lumbar spine phantom.
Figure 5B:
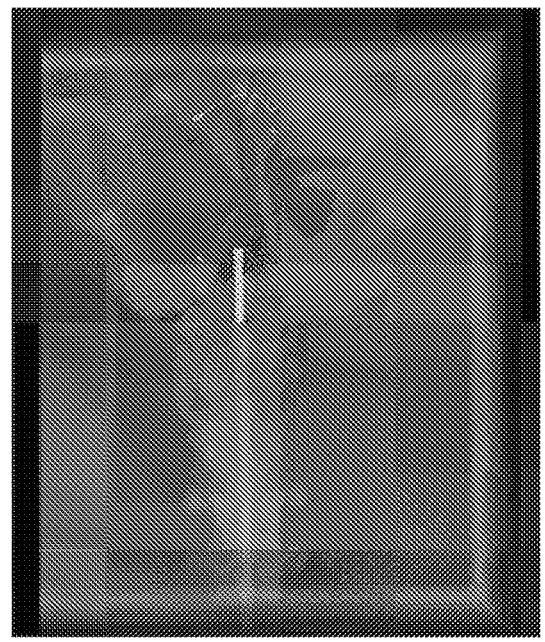
FIG. 5B illustrates the AP image, and the corresponding computed DRR of the 3d pre-operative volume for a isocentric C-arm.
Figure 6A:
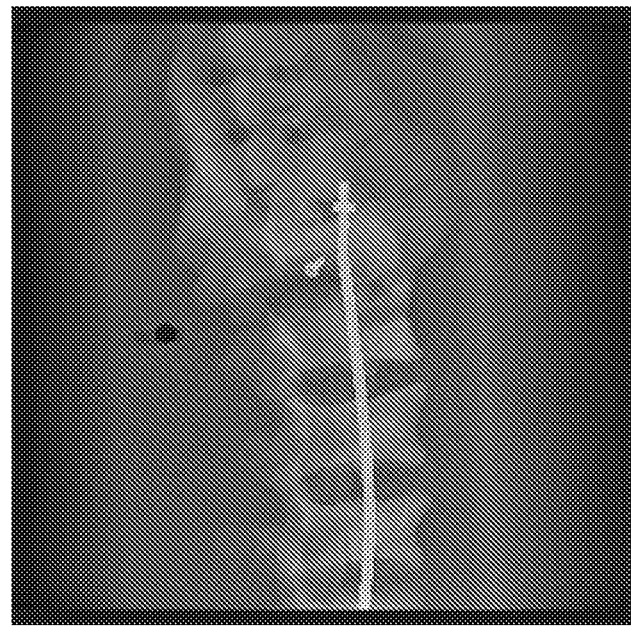
FIG. 6A illustrates the lateral imager shot of a lumbar spine phantom.
Figure 6B:
FIG. 6B illustrates the lateral image, and the corresponding computed DRR of the 3d pre-operative volume for a isocentric C-arm.
Figure 7A:
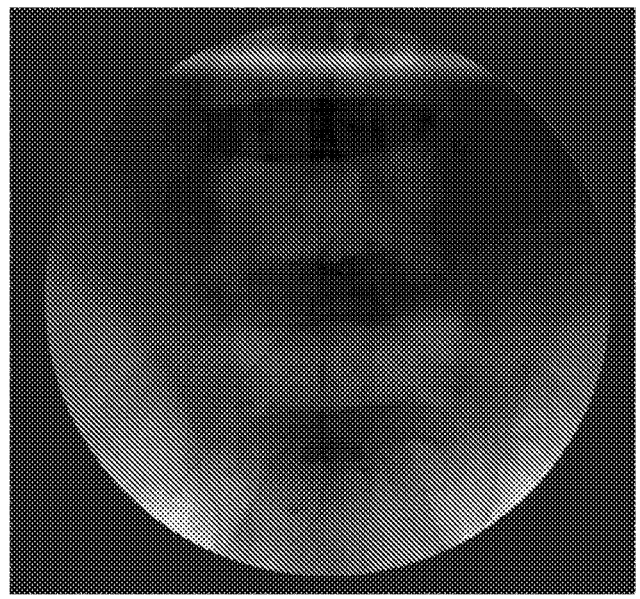
FIG. 7A illustrates the AP (anterio-posterior) imager shot of a lumbar spine phantom for a non-isocentric C-arm.
Figure 7B:
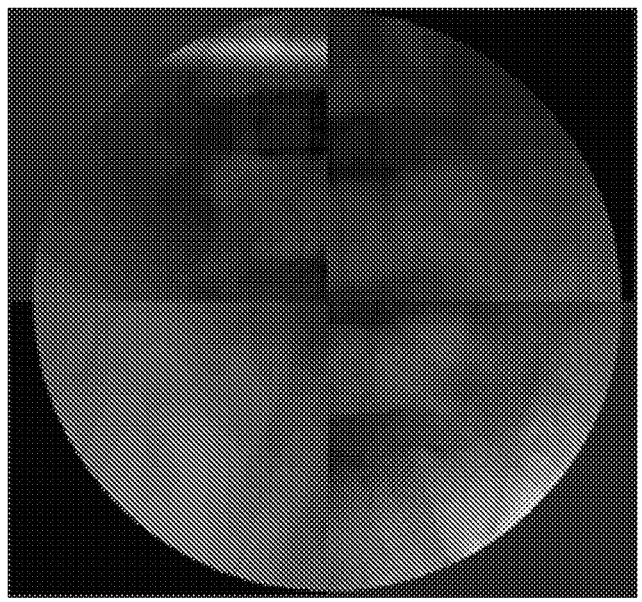
FIG. 7B illustrates the AP image, and the corresponding computed DRR of the 3d pre-operative volume for a non-isocentric C-arm.

The 3D so computed was registered with the pre-operative volume by optimization. Two shots at essential poses such as AP and lateral, were obtained in the surgical routine as shown in FIG. 5A, FIG. 6A and FIG. 7A. The calibration and tracker linking as performed above enabled estimating the projective geometry at the desired pose. For non-isocentric C-arms the positioning was done manually, and involved manual repositioning. A rigid transformation at the specific local region in the anatomy, between pre-operative image and patient body, where the rigidity assumption is valid, given the estimates of the projection geometry, and the shots obtained. A digital radiographic reprojection (DRR) was performed with the pre-operative volume positioned in the canonical coordinate system set up by the spiral object. The registration parameters are the Euler transform that rotates the pre-operative image such that the DRR at the estimated pose is seen to match the obtained shot. This can be setup as a regular 6 DoF optimization problem solved using iterative descent techniques. Further, since the rigid region is bound to be smaller than the full pre-operative volume, a reasonable ROI may be provided with minimal manual input, to constrain the search space and reduce the number of DRRs to be evaluated. The computed DRR images of the 3d pre-operative volume along with the AP image for a isocentric C-arm and a non-isocentric arm are as shown in FIG. 5B, FIG. 6B and FIG. 7B respectively.

Although the detailed description contains many specifics, these should not be construed as limiting the scope of the invention but merely as illustrating different examples and aspects of the invention. It should be appreciated that the scope of the invention includes other embodiments not discussed herein. Various other modifications, changes and variations which will be apparent to those skilled in the art may be made in the arrangement, operation and details of the system and method of the present invention disclosed herein without departing from the spirit and scope of the invention as described here. While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

We claim:

1. A method of providing surgical guidance and targeting in robotic surgery systems comprising an imager comprising a source, a detector having a marker and a navigation system having a tracker, comprising the steps of:
   capturing by an imaging system pre-operative, image data of a patient at predetermined positions and orientations;
   reconstructing a 3D pre-operative image data from the captured pre-operative image data using a processing system;
   capturing 2D intra-operative image data of the patient at the predetermined positions and orientations of the imager during a surgical procedure;
   registering the 2D intra-operative image data and data from the navigation system in real time during the surgical procedure to track the position of a tool;
   registering the 2D intra-operative image data with the 3D pre-operative image data, wherein the registering comprises:
      calibrating one or more intrinsic parameters of the imager;
      performing extrinsic calibration of the imager to localize the detector image plane in 3D with respect to a surgical site, the calibration comprising the steps of:
         capturing two or more images of a space calibration object placed on a surface using the imager, the detector positioned at two or more predetermined locations and orientations, wherein the object comprises a spiral arrangement of reference indices embedded around a radio transparent cylindrical structure and arranged around a camera axis and wherein the space calibration object (307) is a cylindrical object and is placed with a first reference index kept proximal to the tracker and wherein the cylindrical object has a reference marker placed proximal to the first reference index:
   recording the position and displacement of the detector by a tracker attached to the detector, for each image capture;
   identifying the location of the reference indices in each capture, wherein identifying the location of the reference indices is based on image processing techniques selected from thresholding or Hough transform;
computing a projection iteratively from a spiral canonical 3d coordinate system to each of the captured images and obtaining an Euler rotation for each image, wherein computing a projection comprises iterative optimization techniques selected from steepest descent, least-squares minimization, or Frobenius-norm minimization;
   obtaining a transform that links the computed projections and the tracker recorded positions and displacements of the detector; and
   positioning the pre-operative image data in the spiral canonical 3D coordinate system and applying one or more digital radiographic re-projections (DRR) to obtain a 2D projection of the preoperative volume that is aligned with the 2D intra-operative images, wherein the positioning of the pre-operative volume in the spiral canonical 3D coordinate system and applying one or more digital radiographic re-projections (DRR) does not require placement of markers on the patient; and
augmenting the intra-operative image data with a rendering of the 3D pre-operative image data that is in registration with the real time intra—operative 2D image data.

2. The method of claim 1, wherein the imaging system is a C-arm apparatus comprising x-ray modality or ultrasound or both.

3. The method of claim 1, wherein the imaging system comprises a pre-operative, volumetric imaging modality and is selected from CT scan or MRI scan.

4. The method of claim 1, wherein the navigation system is an optical navigation system or an electro-magnetic system.

5. A robotic surgery system comprising:
   an imaging system (320) comprising an imaging modality that is configured to capture pre-operative 2D images of a patient at predetermined positions and orientations and reconstruct a 3D pre-operative image from the obtained 2D images;
   an imager (301) having a source (303), a detector (305), a marker attached to the detector wherein the imager (303) is configured to be fixed at one or more positions and orientations and capture 2D intra-operative image data of a patient during a surgical procedure;
   a navigator system (313) having a tracker configured to obtain navigator data comprising position information of tools;
   a computing system (330) comprising
   a memory module (332) and a processing module (334) coupled to the memory module (332) wherein the processing module (334) is configured to
      register the 2D intra-operative image data and the navigation system data in real time during the surgical procedure to track the position of tools;
      register the 2D intra-operative image data with the 3D pre-operative image, wherein the processing module is configured to:
         calibrate one or more intrinsic parameters of the imager;
         perform extrinsic calibration of the imager to localize the detector image plane in 3D with respect to a surgical site, wherein to perform extrinsic calibration of the imager the processing module is configured to
            capture two or more images of a space calibration object placed on a surface, the detector positioned at two or more predetermined locations and orientations, wherein the object comprises a spiral arrangement of reference indices embedded around a radio transparent cylindrical structure and arranged around a camera axis, wherein the space calibration object (307) is a cylindrical object and is placed with a first reference index kept proximal to the tracker and wherein the cylindrical object has a reference marker near the first reference index:
            record the position and displacement of the detector by a tracker for each image capture;
            identify the location of the reference indices in each capture, wherein to identify the location of the reference indices the processing module is configured to apply image processing techniques selected from thresholding or Hough transform;
            compute a projection iteratively from a spiral canonical 3d coordinate system to each of the captured images and obtain an Euler rotation for each image, wherein to compute a projection the processing module is configured to apply iterative optimization techniques selected from steepest descent, least-squares minimization, or Frobenius-norm minimization; and
            obtain a transform that links the computed projections and the tracker recorded positions and displacements of the detector;
      obtain two or more images of the patient using the imager, the detector positioned at the predetermined locations and orientations;
      register a pre-operative volume by reconstructing a 3D image from the obtained two or more images; and
      position the pre-operative volume in the spiral canonical 3D coordinate system and apply one or more digital radiographic re-projections (DRR) to obtain a 2D projection of the preoperative volume that is aligned with the 2D intra-operative images; and
   augment the 2D intra-operative image data with a rendering of the 3D pre-operative image data that is in registration with the real time intra-operative 2D image data; and
   a display device (340) configured to display the rendering of the 3D pre-operative image data that is in registration with the real time intra-operative 2D image data and the position of the tools.

6. The system of claim 5, wherein the imager is a C-arm apparatus comprising x-ray modality or ultrasound or both.

7. The system of claim 5, wherein imaging modality is selected from CT scan or MRI scan.

8. The system of claim 5, wherein the navigation system is an optical navigation system or an electro-magnetic system.

* * * * *